United States Patent [19]

Ward

[11] 4,443,467
[45] Apr. 17, 1984

[54] ANTIDIARRHOEAL AGENTS

[75] Inventor: Terence J. Ward, Slough, United Kingdom

[73] Assignee: John Wyeth & Brother, Limited, Maidenhead, England

[21] Appl. No.: 262,148

[22] Filed: May 11, 1981

[30] Foreign Application Priority Data

May 27, 1980 [GB] United Kingdom ................ 8017377
Feb. 12, 1981 [GB] United Kingdom ................ 8104410

[51] Int. Cl.$^3$ ................ A61K 31/40; A61K 31/505; A61K 31/415
[52] U.S. Cl. .................................... 424/274; 424/251; 424/273 R
[58] Field of Search .................... 424/274, 273 R, 251

[56] References Cited

FOREIGN PATENT DOCUMENTS 1530675 11/1978 United Kingdom ................ 424/274

Primary Examiner—Frederick E. Waddell

Attorney, Agent, or Firm—Richard K. Jackson

[57] ABSTRACT

Guanidines of formula

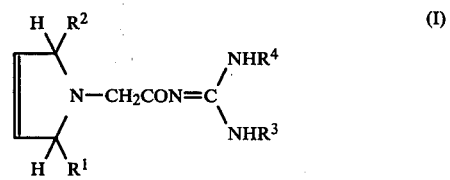

and their pharmaceutically acceptable acid addition salts, (wherein $R^1$ and $R^2$ each represents lower alkyl or trifluoromethyl and $R^3$ and $R^4$ each represents hydrogen or lower alkyl or $R^3$ and $R^4$ together represent dimethylene or trimethylene) are useful in treating or preventing diarrhoea in mammals or poultry. The compound, if desired, may be administered with one or more antimicrobial, adsorbent, anti-emetic, parasympatholytic or antihistaminic agents.

3 Claims, No Drawings

ANTIDIARRHOEAL AGENTS

This invention relates to antidiarrhoeal agents.

Antidiarrhoeal agents are of value, for example, in the treatment of acute non-infective diarrhoea, chronic diarrhoea caused by functional states such as irritable bowel syndrome and the reduction of the volume of ileostomy discharge. In addition antidiarrhoeal agents are useful adjuncts to more specific measures in providing symptomatic control of chronic diarrhoea associated with inflammatory bowel disease. The class of antidiarrhoeal drugs of most use are the anti-motility agents and of these the three drugs most commonly used are codeine phosphate, diphenoxylate and loperamide. All three possess the disadvantage that they are opioid drugs and possess central narcotic activity especially at high dosages. In addition, codeine phosphate and diphenoxylate have the disadvantage that some degree of tolerance to their constipating effect may develop. Accordingly a need exists for an antidiarrhoeal agent which does not possess such disadvantages.

The antidiarrhoeal agents of the present invention are guanidine derivatives of the general formula

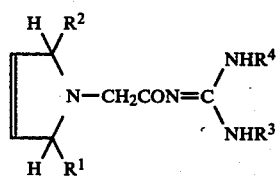

and pharmaceutically acceptable acid addition salts thereof wherein $R^1$ and $R^2$ which may be the same or different represent lower alkyl or trifluoromethyl and $R^3$ and $R^4$ which may be the same or different represent hydrogen or lower alkyl or $R^3$ and $R^4$ together represent dimethylene or trimethylene such that

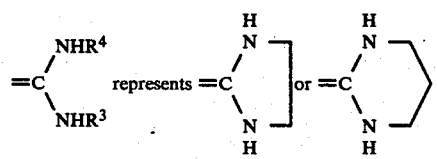

The term "lower" as used herein means that the radical referred to contains 1 to 6 carbon atoms. Preferably the radical contains 1 to 4 carbon atoms.

According to the present invention there is provided a method of treating or preventing diarrhoea in mammals or poultry which comprises administering to an animal in need thereof an amount effective for treating or preventing diarrhoea of a guanidine of formula (I) (as hereinabove defined) or a pharmaceutically acceptable acid addition salt thereof. The animal is preferably a mammal. The mammal may be, for example, cattle, sheep, swine, rabbit, dog, cat, monkey or the like, but it is preferably a human.

Processes for preparing the compounds of general formula (I) and their pharmaceutically acceptable salts are described in U.K. Specification No. 1,530,675.

For example, a reactive derivative of an acid of general formula (II)

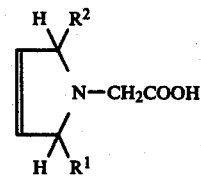

(where $R^1$ and $R^2$ have the meanings given above) or an acid addition salt thereof may be reacted with a compound of general formula (III)

(where $R^3$ and $R^4$ have the meanings given above) and if desired converting a base of general formula (I) into a pharmaceutically acceptable salt thereof. The reactive derivative of the acid of general formula (II) may be, for example, an acid chloride or, preferably, an ester particularly a lower alkyl ester. An alternative method of preparing the antidiarrhoeal agents comprises hydrolysing a nitrile of general formula (IV)

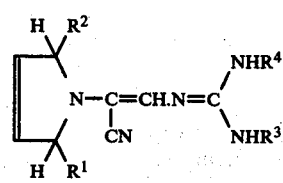

(where $R^1$, $R^2$, $R^3$ and $R^4$ have the meanings given above) and if desired, converting a resulting base of general formula (I) into a pharmaceutically acceptable acid addition salt thereof.

In a further method of preparing the antidiarrhoeal agents in which $R^3$ and $R^4$ are hydrogen or lower alkyl an isothiourea derivative of general formula

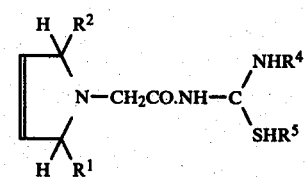

(where $R^1$ and $R^2$ are as defined above, $R^4$ is hydrogen or lower alkyl and $R^5$ is lower alkyl, preferably methyl) is reacted with ammonia or an amine of formula $R^3NH_2$ (VI) (where $R^3$ is hydrogen or lower alkyl) and, if desired, converting a resulting base of general formula (I) into a pharmaceutically acceptable acid addition salt thereof. An alternative method for preparing the agents in which $R^3$ is hydrogen or lower alkyl and $R^4$ is hydrogen comprises reacting an acylcyanamide of general formula (VII)

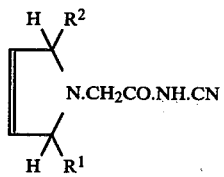

(VII)

(where $R^1$ and $R^2$ are as defined above) with ammonia or an amine of formula (VI) above and, if desired, converting a resulting base into a pharmaceutically acceptable acid addition salt thereof.

Antidiarrhoeal agents in which $R^3$ and $R^4$ are hydrogen may be prepared by a still further method which comprises condensing a dihydropyrrole of general formula (VIII)

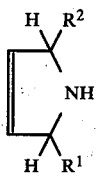

(VIII)

(where $R^1$ and $R^2$ are as defined above) with a haloacetylguanidine of general formula $$HalCH_2CON=C\begin{matrix}NH_2\\ \\NH_2\end{matrix}$$

(where Hal is chlorine or bromine) and, if desired, converting a resulting base of general formula (I) into a pharmaceutically acceptable acid addition salt thereof.

A further method of preparing the anti-diarrhoeal agents comprises reducing a pyrrole derivative of general formula (IX)

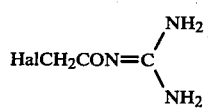

(IX)

(where $R^1$, $R^2$, $R^3$ and $R^4$ have the meanings given above) and, if desired, converting a resulting base of general formula (I) into a pharmaceutically acceptable acid addition salt thereof. The reduction may be carried out with, for example, a dissolving metal reducing agent, for example, zinc in acetic acid.

In the compounds of general formula (I) $R^1$ and $R^2$ can be lower alkyl (for example, methyl, ethyl, propyl or butyl) or trifluoromethyl. Preferably both $R^1$ and $R^2$ are lower alkyl (e.g. methyl). $R^3$ and $R^4$ when taken independently can be hydrogen or lower alkyl (for example, methyl, ethyl, propyl or butyl). Preferably both $R^3$ and $R^4$ are hydrogen.

The antidiarrhoeal agents of the invention have been illustrated in general formula (I) as existing in the acylimino form but it is possible that the compounds exist in other tautomeric forms or mixtures of such forms as explained in further detail in U.K. Patent Specification No. 1,530,675. Where in this specification there is used a name or formula implying any particular tautomeric form it is to be understood that the name or formula includes any other alternative form or a mixture of such forms.

The compounds of the invention contain asymmetric carbon atoms and hence can exist in more than one isomeric form. Such forms can be obtained or separated by standard procedures. For example, the compounds of general formula II in which $R^1$ and $R^2$ are both trifluoromethyl or identical lower alkyl groups can exist in cis or trans forms. Either the cis or the trans form can be obtained by suitable choice of starting material in the processes hereinbefore described. The trans form will normally be obtained as a racemate of the d- and l-enantiomorphs which can be separated by standard methods of resolution if desired. (I) The compounds of general formula (I) in which $R^1$ and $R^2$ are different lower alkyl groups or one is trifluoromethyl and the other lower alkyl contain two asymmetric carbon atoms and hence can exist in four optically active forms. Normally the compounds are prepared in the form of racemates which can, if desired, be resolved by standard methods.

Examples of pharmaceutically acceptable acid addition salts are those derived from inorganic and organic acids such as sulphuric, hydrochloric, hydrobromic, phosphoric, tartaric, fumaric, maleic, citric, acetic, formic, methanesulphonic and p-toluenesulphonic acids.

A particularly preferred antidiarrhoeal agent of the present invention is N-diaminomethylene-(trans-2,5-dihydro 2,5-dimethyl-1H-pyrrol-1-yl)acetamide or a pharmaceutically acceptable acid addition salt thereof. The preferred compound is a compound of formula (I) wherein $R^1$ and $R^2$ have the preferred meanings of methyl and $R^3$ and $R^4$ have the preferred meanings of hydrogen.

The antidiarrhoeal activity of the agents of the present invention was demonstrated by the effect on castor oil-induced diarrhoea in rats. A representative agent of the present invention, N-diaminomethylene-(trans-2,5-dimethyl-1H-pyrrol-1-yl)acetamide, was compared with the commercial agent loperamide. In the procedure 6 groups of male rats weighing approximately 150 g, were fasted overnight and placed in separate cages. The rats were dosed orally with either hydroxypropylmethyl cellulose/saline or the test drugs at doses ranging from 30 mg/kg to 3 mg/kg. 1 hour later each rat was given 1.0 ml castor oil orally to induce diarrhoea. Faecal output was collected on pre-weighed papers beneath each cage and weighed at intervals during the subsequent 6 hour experimental periods. The results of the testing are given below:

| Compound | Dose mg/kg p.o. | Inhibition of faecal output | |
|---|---|---|---|
| | | 0–2 hours | 0–6 hours |
| N—diaminomethylene- (trans-2,5-dihydro- 2,5-dimethyl-1H— pyrrol-1-yl)aceta- mide | 30 | 100% (XX) | 99% (XX) |
| | 10 | 100% (XX) | 86% (X) |
| | 3 | 100% (XX) | 58% (N.S.) |
| loperamide | 30 | 98% (XX) | 97% (XX) |
| | 10 | 100% (XX) | 99% (XX) |
| | 3 | 96% (XX) | 77% (XX) |

XX = P < 0.01
X = P < 0.05
N.S. = P > 0.05

The above results indicate that N-diaminomethylene-(trans-2,5-dihydro-2,5-dimethyl-1H-pyrrol-1-yl)acetamide gives marked protection against diarrhoea at 3 mg/kg and above.

The results of testing N-diaminomethylene-(cis-2,5-dihydro-2,5-dimethyl-1H-pyrrol-1-yl)acetamide in the above procedure are given below:

| Dose | Inhibition of faecal output | |
|---|---|---|
| mg/kg p.o. | 0-2 hours | 0-6 hours |
| 30 | 100% (XX) | 99% (XX) |
| 10 | 100% (XX) | 34% (N.S.) |
| 3 | 100% (XX) | 50% (N.S.) |

The absence of central narcotic activity of N-diaminomethylene-(trans-2,5-dihydro-2,5-dimethyl-1H-pyrrol-1-yl) acetamide was demonstrated in another procedure involving the effect of naloxone on the antidiarrhoeal activity of the test compound (either the agent of the present invention or codeine phosphate). In this procedure 6 groups of male rats were fasted overnight and dosed as follows:

Group A hydroxypropylmethylcellulose/saline per os.
Group B hydroxypropylmethylcellulose/saline per os; naloxone 5 mg/kg sub-cut.
Group C N-diaminomethylene-(trans-2,5-dihydro-2,5-dimethyl-1H-pyrrol-1-yl)acetamide 30 mg/kg per os.
Group D N-diaminomethylene-(trans-2,5-dihydro-2,5-dimethyl-1H-pyrrol-1-yl)acetamide 30 mg/kg per os; naloxone 5 mg/kg sub-cut.
Group E codeine phosphate, 30 mg/kg per os.
Group F codeine phosphate, 30 mg/kg per os; naloxone 5 mg/kg sub-cut.

Naloxone was administered 30 minutes after the test drugs, and after a further 30 minutes each rat was given castor oil (1.0 ml per os). Faecal output was measured throughout the subsequent 6 hour period. The results of this procedure are given below:

| Drug treatment | Inhibition of faecal output | |
|---|---|---|
| | 0-2 hours | 0-6 hours |
| A. Control | — | — |
| B. Control + naloxone | -6% (N.S.) | -11% (N.S.) |
| C. N—diaminomethylene-(trans-2,5-dihydro-2,5-dimethyl-1H—pyrrol-1-yl)acetamide (30 mg/kg) | 100% (XX) | 82% (XX) |
| D. N—diaminomethylene-(trans-2,5-dihydro-2,5-dimethyl-1H—pyrrol-1-yl)acetamide (30 mg/kg) + naloxone | 100% (XX) | 75% (XX) |
| E. Codeine phosphate (30 mg/kg) | 90% (XX) | 54% (XX) |
| F. Codeine phosphate (30 mg/kg) + naloxone | 22% (N.S.) | 29% (X) |

XX = P < 0.01
X = P < 0.05
N.S. = P < 0.05

These results show that naloxone per se had no effect on faecal output (see Groups A and B) and did not block the antidiarrhoeal effect of N-diaminomethylene-(trans-2,5-dihydro-2,5-dimethyl-1H-pyrrol-1-yl)acetamide (see Groups C and D) indicating that the agent of the present invention does not act at opiate receptors. In contrast Groups E and F show that the presence of naloxone prevented the antidiarrhoeal effect of codeine phosphate, especially in the early part of the experiment.

In another test for antidiarrhoeal activity 4 groups of male rats were placed in individual cages with food and water ad libitum. They were dosed daily for 5 days with either hydroxypropylmethylcellulose/saline or N-diaminomethylene-(trans-2,5-dihydro-2,5-dimethyl-1H-pyrrol-1-yl)-acetamide at 30 mg/kg. Faecal output was measured 3 hours, 7 hours and 24 hours after each dose. The results are shown in the table below:

| Time after dosing | Inhibition of faecal output | | | | |
|---|---|---|---|---|---|
| | Day 1 | Day 2 | Day 3 | Day 4 | Day 5 |
| 0-3 h. | 74% N.S. | 90% * | 82% ** | 90% ** | 93% * |
| 0-7 h. | 7% N.S. | 59% N.S. | 50% N.S. | 27% N.S. | 16% N.S. |
| 0-24 h. | 23% N.S. | 3% N.S. | 13% N.S. | 10% N.S. | Not recorded |

** = P < 0.01
* = P < 0.05
N.S. = P > 0.05

From these results it is clear that the agent of the present invention gave a consistent inhibition of defaecation in the first 3 hours after dosing on each day at 30 mg/kg. There was no evidence that the daily dosing caused either tolerance or potentiation of effect to occur.

The active ingredients of the present invention may be administered alone or in the form of a pharmaceutical composition. The pharmaceutical compositions comprise a guanidine of general formula (I) or a pharmaceutically acceptable salt thereof in association with a pharmaceutically acceptable carrier. The compositions may be prepared by a process which comprises bringing the acive ingredient into association with the carrier (e.g. by mixing). Any suitable carrier known in the art can be used to prepare the pharmaceutical composition. In such a composition, the carrier is generally a solid or liquid, or a mixture of a solid and a liquid.

Solid form compositions include powders, granules, tablets and capsules (e.g. hard and soft gelatin capsules). A solid carrier can be, for example, one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99% preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups and elixirs. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral administration include water (particularly containing additives as above e.g. cellulose derivatives, preferably sodium carboxymethyl cellulose solution), alcohols (including monohydric alcohols and polyhydric alcohols, e.g. glycerol and glycols) and their derivatives, and oils (e.g. fractionated coconut oil and arachis oil).

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. The quantity of the active ingredient in a unit dose of composition may be varied or adjusted from 0.5 mg. or less to 750 mg. or more, according to the particular need and the activity of the active ingredient.

The dosage of the present agents will vary with the form of administration and the particular compound chosen. Furthermore, it will vary with the particular subject under treatment. Treatment may be initiated with small dosage substantially less than the optimum dose of the compound. Thereafter, the dosage may be increased by small increments until the optimum effect under the circumstances is reached. In general, the compounds of this invention are most desirably administered at a concentration level that will generally afford effective results without causing any harmful or deleterious side effects. In general a dose of 1 to 200 mg of the agent should be suitable for an average adult. Preferred oral recommended amounts are 1 to 50 mg. particularly 2 to 25 mg.

Diarrhoea is often associated with infections and in such cases it may be advantageous to administer the anti-diarrhoeal agent of the present invention together with an antimicrobial agent such as an antibacterial or antiprotazoal agent. The antibacterial agent may be, for example, an antibiotic such as neomycin, streptomycin or dihydrostreptomycin or a sulpha drug such as phthalylsulphathiazole. More than one antibacterial agent may be employed in the composition. Antiprotazoal agents are particularly employed with diarrhoea associated with amoebiasis. Examples of antiprotazoal agents include metronidazole, acetarsol, chloroquine, cliquinol and tetracycline. The antidiarrhoeal agents of the invention may also be administered with an adsorbent (e.g. a clay such as an attupulgite, particularly an activated attupulgite, or kaolin, pectin or, for example, a mixture of kaolin and pectin). These adsorbents help to adsorb toxins which may be associated with a diarrhoeal attack. Vomiting can accompany diarrhoea and therefore the antidiarrhoeal agent of the present invention may be administered together with an antiemetic, e.g. cyclizine. Antidiarrhoeal agents can be given for the treatment or prophylaxis of travellers' diarrhoea and for this purpose the anti-diarrhoeal agents of the present invention can be administered together with a parasympatholytic or antihistaminic agent (e.g. atropine, hyoscine) useful in the prevention or treatment of motion sickness.

Accordingly the invention also provides a pharmaceutical composition comprising a guanidine of general formula (I) or a pharmaceutically acceptable salt thereof and one or more antimicrobial, adsorbent, antiemetic, parasympatholytic or antihistaminic agents in association with a pharmaceutical carrier.

The following Examples 1 to 14 illustrate the preparation of pharmaceutical compositions containing the active ingredients of the present invention. Examples 15 and 16 illustrate the preparation of the antidiarrhoeal agents.

EXAMPLE 1

| Capsules | mg/capsule |
| --- | --- |
| N—Diaminomethylene-(trans-2,5-dihydro-2,5-dimethyl-1H—pyrrol-1-yl)acetamide dihydrochloride | 6.86 |
| Lactose B.P. | 71.79 |
| Maize starch, dried B.P. | 80.00 |
| Aerosil 200 (colloidal silicon dioxide) | 0.90 |
| Magnesium stearate, B.P. | 0.45 |
| | 160.00 |

Capsules of the above are made by thoroughly mixing together batches of the above ingredients and filling hard gelatine capsules with the mixture.

EXAMPLE 2

| Tablets | mg/tablet |
| --- | --- |
| N—Diaminomethylene-(trans-2,5-dihydro-2,5-dimethyl-1H—pyrrol-1-yl)acetamide dihydrochloride | 6.86 |
| Lactose B.P. | 60.89 |
| Avicel pH101 (microcrystalline cellulose) | 30.00 |
| Amberlite IRP 88 (potassium salt of a cation exchange resin of the carboxylic type) | 2.00 |
| Magnesium stearate B.P. | 0.25 |
| | 100.00 |

Tablets of the above composition are made by mixing batches of the ingredients and compressing the mixture to form tablets.

EXAMPLE 3

| Tablets | mg/tablet |
| --- | --- |
| N—Diaminomethylene-(trans-2,5-dihydro-2,5-dimethyl-1H—pyrrol-1-yl)-acetamide dihydrochloride | 6.86 |
| Neomycin sulphate | 350.00 |
| Avicel pH 101 | 80.00 |
| Lactose B.P. | 50.70 |
| Amberlite IRP 88 | 10.00 |
| Magnesium stearate B.P. | 2.50 |
| | 500.00 |

Tablets of the above composition are made by mixing batches of the ingredients and compressing the mixture to form tablets.

EXAMPLES 4 TO 9

Tablets of the following compositions are made by the blending batches of the ingredients and compressing the mixture to form tablets:

| Ingredients | Example No. | | | | | |
|---|---|---|---|---|---|---|
| | 4 | 5 | 6 | 7 | 8 | 9 |
| N—Diaminomethylene-(trans-2,5-dihydro-2,5-dimethyl-1H—pyrrol-1-yl)acetamide dihydrochloride | 6.86 | 6.86 | 6.86 | 6.86 | 6.86 | 6.86 |
| Avicel PH 101 (microcrystalline cellulose BPC) | 109.89 | 109.89 | 100.00 | 100.00 | 30.00 | — |
| Lactose BP | 100.00 | 100.00 | 81.89 | 80.06 | 60.46 | — |
| Amberlite IRP 88 | 7.00 | 7.00 | 9.00 | 5.00 | 2.00 | 8.00 |
| Magnesium stearate BP | 1.25 | 1.25 | 2.25 | 1.25 | 0.25 | 1.00 |
| Streptomycin sulphate BP | 125.00 | — | — | — | — | — |
| Dihydrostreptomycin sulphate (BP 1958) | — | 125.00 | — | — | — | — |
| Metronidazole BP | — | — | 250.00 | — | — | — |
| Cyclizine hydrochloride BP | — | — | — | 56.83 | — | — |
| Hyocine hydrobromide BP | — | — | — | — | 0.43 | — |
| Starch BP | — | — | — | — | — | 22.14 |
| Pre gelatinised maize starch BP | — | — | — | — | — | 12.00 |
| Attapulgite, activated | — | — | — | — | — | 350.00 |
| | 350.00 mg | 350.00 mg | 450.00 mg | 250.00 mg | 100.00 mg | 400.00 mg |

EXAMPLES 10 TO 14

Capsules of the following compositions are made by blending batches of the ingredients and filling the mixed powders into hard gelatin capsules on a filling machine.

| Ingredients | Example No. | | | | |
|---|---|---|---|---|---|
| | 10 | 11 | 12 | 13 | 14 |
| N—Diaminomethylene-(trans-2,5-dihydro-2,5-dimethyl-1H—pyrrol-1-yl)acetamide dihydrochloride | 6.86 | 6.86 | 6.86 | 6.86 | 6.86 |
| Lactose BP | 60.00 | 60.00 | 43.17 | 71.36 | 89.77 |
| Maize Starch BP | 56.27 | 56.27 | 51.79 | 80.00 | 100.00 |
| Aerosil 200 | 1.25 | 1.25 | 0.90 | 0.90 | 2.25 |
| Magnesium Stearate BP | 0.62 | 0.62 | 0.45 | 0.45 | 1.12 |
| Streptomycin sulphate BP | 125.00 | — | — | — | — |
| Dihydrostreptomycin sulphate (BP 1958) | — | 125.00 | — | — | — |
| Cyclizine hydrochloride BP | — | — | 56.83 | — | — |
| Hyocine hydrobromide BP | — | — | — | 0.43 | — |
| Metronidazole BP | — | — | — | — | 250.00 |
| | 250.00 mg | 250.00 mg | 160.00 mg | 160.00 mg | 450.00 mg |

EXAMPLE 15

N-Diaminomethylene-(trans-2,5-dihydro-2,5-dimethyl-1H-pyrrol-1-yl)acetamide

A solution of guanidine hydrochloride (2.3 g., 0.024 mol) and sodium ethoxide (from 0.55 g, 0.024 mol of sodium) in absolute ethanol (24 cm³) was stirred at room temperature for 1 h. The precipitated sodium chloride was removed by filtration and washed with ethanol (4 cm³). Methyl (trans-2,5-dihydro-2,5-dimethyl-1H-pyrrol-1-yl)acetate (3.4 g., 0.02 mol) was added to the combined filtrate and washings obtained above and the solution stoppered and stirred for 18 h. The reaction mixture was then evaporated and the residue crystallised from ethanol to give the product (1.25 g.). The base was suspended in ethanol and acidified with ethanolic hydrogen chloride, the clear solution thus obtained was diluted with ethyl acetate and concentrated by evaporation to precipitate the title compound as the dihydrochloride (1.6 g.) m.p. 210°–11° C.(d).

EXAMPLE 16

N-Diaminomethylene-(cis-2,5-dihydro-2,5-dimethyl-1H-pyrrol-1-yl)acetamide

A mixture of guanidine hydrochloride (0.6 g.) sodium methoxide (from 0.138 g. of sodium), and methanol (5 cm³) was stirred at room temperature for 1 hour. Methyl cis-(2,5-dimethyl-2,5-dihydropyrrol-1-yl)acetate was then added (0.6 g.) and the mixture stirred overnight (16 h.). The solution was then evaporated and the residue partitioned between water (1.5 cm³) and ether (3 cm³). After stirring at 0° C. for about 3 hours a white precipitate separated. The precipitate was collected and washed with water and ether to give 0.24 g. of title base. The base was dissolved in isopropyl alcohol (3 cm³) and acidified with ethanolic hydrogen chloride. On cooling in ice the title compound hydrochloride was collected and washed with isopropyl alcohol. The product was then dissolved in hot ethanol (3 cm³) diluted with ethyl acetate (2 cm³) and cooled to give pure title compound as the hydrochloride (0.15 g.), m.p. 207°–9° C.

I claim:

1. A method of treating or preventing diarrhoea in mammals or poultry which comprises administering to an animal in need thereof an amount effective for treating or preventing diarrhoea of a guanidine of formula (I)

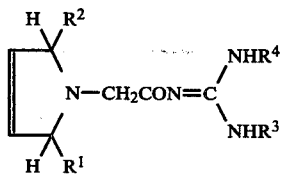 (I)

or a pharmaceutically acceptable acid addition salt thereof, wherein $R^1$ and $R^2$ each represents lower alkyl or trifluoromethyl and $R^3$ and $R^4$ each represents hydrogen or lower alkyl or $R^3$ and $R^4$ together represent dimethylene or trimethylene.

2. A method as claimed in claim 1 wherein the guanidine is N-diaminomethylene-(trans-2,5-dihydro-2,5-dimethyl-1H-pyrrol-1-yl)acetamide or a pharmaceutically acceptable acid addition salt thereof.

3. A method of treating or preventing diarrhoea in mammals as claimed in claim 1 which comprises administering to a mammal in need thereof a dose of 1 to 200 mg. of N-diaminomethylene-(trans-2,5-dihydro-2,5-dimethyl-1H-pyrrol-1-yl)acetamide or a pharmaceutically acceptable acid addition salt thereof.

* * * * *